(12) United States Patent
Boesch et al.

(10) Patent No.: US 6,528,025 B1
(45) Date of Patent: Mar. 4, 2003

(54) PROCESS OF MANUFACTURING EQUIPMENT FOR PREPARING ACETALS AND KETALS

(75) Inventors: Volkmar Boesch, Loerrach (DE); Juan Ramon Herguijuela, Auggen (DE)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/606,918

(22) Filed: Jun. 29, 2000

(30) Foreign Application Priority Data

Jun. 26, 2000 (EP) ............................. 00113463

(51) Int. Cl.⁷ ..................... B01J 10/00; B01D 15/00; F28D 8/04; C07C 43/30
(52) U.S. Cl. ................. 422/189; 210/640; 422/198; 422/190; 568/591
(58) Field of Search .................... 210/640; 422/198, 422/189, 190; 568/591

(56) References Cited

U.S. PATENT DOCUMENTS

| | | | |
|---|---|---|---|
| 4,775,447 A | * 10/1988 | Hsu | 203/62 |
| 5,156,740 A | 10/1992 | Brüschke | |
| 5,866,654 A | * 2/1999 | Fuss et al. | 525/56 |
| 5,892,129 A | 4/1999 | Hoepp et al. | |

FOREIGN PATENT DOCUMENTS

| | | |
|---|---|---|
| DE | 29 29 827 | 2/1981 |
| EP | 0 096 339 B2 | 5/1983 |
| WO | WO 95/07915 | 3/1995 |
| WO | WO 99/47484 | 9/1999 |

OTHER PUBLICATIONS

Kuznetsov et al., Separation of water–alcohol mixtures by composite pervaporation membranes, 1998, 71 (9), 1508–1513.*

Waldburger, et al., "Membrane Reactors in Chemical Production Processes and the Application to the Prevaporation–Assisted Esterification," *Chem. Eng. Technol.* 19, pp. 117–126 (1996).

S. Bittlich, et al., "Enhancement of the Conversion of Esterification Reactions by Non–porous Membranes," in Proceedings of the Fifth International Conference on Pervaporation Processes in the Chemical Industry, Ed. R. Bakish, pp. 273–281 (Mar. 1991).

Product Specification—Sulzer Chemtech (20.01.06.40–V11.99–70).

Derwent English language abstract of DE 29 29 827 (document B2 above).

* cited by examiner

*Primary Examiner*—Jafar Parsa
(74) *Attorney, Agent, or Firm*—Bryan Cave LLP

(57) ABSTRACT

A process for the preparation of acetals and ketals by reacting an aldehyde or Ketone with an alcohol in the presence of solid acid and removing water by pervaporation. Manufacturing equipment for the preparation of acetals and ketones is also provided.

2 Claims, 1 Drawing Sheet

1, 4, 7 - REACTOR WITH ACID ION EXCHANGE RESIN
2, 5, 8 - VESSEL WITH BASIC ION EXCHANGE RESIN
3, 6, 9 - PERVAPORATION UNIT

PROCESS OF MANUFACTURING EQUIPMENT FOR PREPARING ACETALS AND KETALS

The present invention is concerned with a novel process for preparing acetals and ketals. As is known, acetals and ketals can be prepared by reacting an aldehyde or ketone with an alcohol in the presence of an acidic catalyst. However, the reaction is reversible and, at ambient temperature or above, the equilibrium of the reaction is shifted to the side of the starting materials, acetal or ketone, and alcohol.

The invention provides a novel process for the continuous preparation of acetals and ketals in concentrated form and avoids energy-intensive destination procedures of conventional manufacturing processes, which are often rendered difficult by the formation of azeotropes.

Thus, the invention is concerned with a process for the preparation of acetals or ketals which comprises reacting an aldehyde or ketone with an alcohol in the presence of solid acid and removing water from the reaction product by pervaporation.

More specifically, the present invention is concerned with a process for recovering acetals or ketals from reaction mixtures obtained by reacting an aldehyde or ketone with an alcohol, particularly by reaction of a lower aliphatic aldehyde or ketone with a lower aliphatic alcohol or sugar alcohol, in the presence of an acid which process comprises subjecting the reaction mixture containing an acetal or ketal together with water and unreacted aldehyde or ketone and alcohol, to treatment with a base followed by pervaporation.

In the following, the term "ketal" and "ketalisation" will be used to simultaneously denote acetals and acetalisation, respectively. The term "ketone" includes ketones and aldehydes. The term "lower" as used herein denotes compounds having 1 to 7 carbon atoms. Examples of lower aliphatic ketones are acetone and methyl ethyl ketone. Examples of lower aliphatic aldehydes are formaldehyde, acetaldehyde, propionic aldehyde, butyric aldehyde and isobutyric aldehyde. Examples of alcohols are methanol and ethanol. Sorbose is an example of a sugar alcohol.

Pervaporation is a known method for separating liquids from mixtures thereof, e.g., for separating water from mixtures with organic liquids, such as alcohols, aldehydes or ketones, see, e.g., European Patent No. 0 096 339, and Chem.Eng.Technol. 19 (1996) 117–126. In pervaporation processes, the different ability of liquids or gases to permeate polymer membranes is used to separate mixtures thereof While pervaporation has been proposed to separate water e.g., from esterification reactions, the successful application of this method to remove reaction water from acetalisation or ketalisation processes has, so far, not been reported. This is not surprising since in ketalisation reactions the reaction product is in equilibrium with the starting ketone and alcohol, and low temperatures are required to shift the equlibrium to the side of the ketal. Pervaporation processes, to be carried out efficaciously, require elevated temperatures where the equilibrium of the ketalisation reaction is shifted markedly to the side of the starting materials of the reaction.

In a preferred embodiment the process of this invention is carried out in a number of consecutive steps. In a first step, an alcohol is reacted with an aldehyde or ketone in the presence of a solid acid to obtain an equilibrium mixture comprising the reactants, the desired ketal, and water. In a second step, the equilibrium mixture obtained is subjected to treatment with a solid base followed by pervaporation. In a third step the pervaporation retentate is subjected to treatment with a solid acid under conditions that favour ketalisation. In a fourth step, the product from the third step treated with a solid base followed by pervaporation. The removal of water from the pervaporation retentate is repeated until the ketal is obtained in the desired purity which is determined by the requirements of the ultimate use of the ketal, i.e. by the requirements of the reactions wherein the ketal is processed further.

The process of this invention can be applied to any ketalisation reaction. Examples of such reactions are
Conversion of acetone to 2,2-dimethoxy propane;
Conversion of methyl ethyl ketone to dimethoxy butane;
Conversion of sorbose to sorbose diacetonide;
Conversion of butendiol to isopropoxy dioxepen;
Conversion of methyl glyoxal to dimal.

In a more preferred aspect, the process of this invention is used to prepare 2,2-dimethoxy propane from acetone and methanol.

In the first step of the reaction in accordance with the invention the solid acid is suitably a strongly acidic polymer such as a polystyrene sulfonic acid, which may be macroporous or gel-type. Ion exchange resins conventionally used to catalyze ketalisation reactions can be used. Examples of such ion exchange resins are Dowex 50 (Dow Chemical), Amberlite IR 120, Amberlyst A 15 and A 36 (Rohm & Haas), Lewatit (Bayer). The reaction temperature is suitably from about −50° to about 10° C., preferably from about −35° to about −40° C.

Examples of bases as used in the second reaction step are weakly basic ion exchange resins such as polystyrenes resins carrying quaternary ammonium groups, e.g. IRA 96 (Rohm & Haas).

For the pervaporation, any membrane which is resistent to the reaction products and which are permeable for water may be used. Examples of such membranes are hydrophilic membranes which may be polymer or ceramic membranes. Polymer membranes may be composite membranes comprising a support layer, e.g. on the basis of acrylnitril polymers, and a polyvinyl alcohol layer which provides the actual active separating layer. Examples of membranes useful in the process of this invention are membranes provided by Sulzer Chemtech GmbH, D-66540 Neunkirchen, Germany under the name Pervap 1055, Pervap 2000 and Pervap 2510; as well as membranes provided by CM-CELFA Membrantechnik AG, CH-6423 Seewen, Switzerland, under the name CMC-CE-02 and CM-CE-01.

The pervaporation is suitably carried out at elevated temperatures, i.e., temperatures up to the boiling point of the reaction mixture on the retentate side of the membrane. In general, the pervaporation is carried out at about 600 to about 130° C. The pressure in the pervaporation is not critical and is basically determined by the pressure required to sustain the mass flow. However elevated pressure, e.g., up to 4 Bar on the retentate side of the membrane can be used, subject to the mechanical resistance of the membrane, to increase the boiling point of the reaction mixture, thus allowing the pervaporation to proceed at higher temperature. The pressure on the permeate side of the membran is suitably about 1 to about 500 mBar.

BRIEF DESCRIPTION OF THE DRAWINGS

The invention is further illustrated by FIG. 1 which provides a mass flow scheme for obtaining substantially pure 2,2-dimethoxy propane from acetone and methanol, but which may find use for other ketals according to the invention.

According to the process in FIG. 1, a mixture of aceton and methanol in a molar ratio of about 2 to about 6 moles, preferably about 4 moles of acetone to one mole of methanol is cooled and fed into reactor 1 which contains an acid ion exchange resin. Reactor 1 is cooled to an appropriate temperature favouring ketal formation, e.g., to a temperature of from about −35 to about −40° C. The flow of the reaction mixture is regulated to allow the reaction mixture to achieve the state of the equilibrium. Depending on the dimension of the reactor the mean residence time of the reaction mixture may vary between 1 and 10 minutes. The reaction product exiting reactor 1 and containing the desired product, 2,2-dimethoxy propane, in admixture with water, aceton and methanol is then fed through vessel 2 which contains a basic ion exchange resin into a pervaporation unit 3. Suitably, a heat exchange device and a heater is provided between 2 and 3 (not shown in FIG. 1) to allow heat transfer from the aceton/methanol mixture to reaction product exiting 2 and to adjust the temperature required for the pervaporation (about 60 to 70° C.). The permeate from the pervaporation unit 3 consists of methanol, water, minor amounts of aceton and traces of ketal. Retentate from the pervaporation unit 3 containing ketal, aceton, methanol and water that was not fully removed in pervaporation unit 3 is cooled to a temperature of from about −35 to about −40° C. and fed into reactor 4 where it is allowed to achieve the state of equilibrium. The reaction mixture then proceeds via basic ion exchange resin bed 5, suitably passing a heat exchange device as in the first reaction step, to pervaporation unit 6. The process of adjusting the equilibrium of the retentate at low temperature and submitting the product again to pervaporation may be repeated as shown (7, 8, 9). While

As will be apparent from the above, the ketalisation reaction is carried out at low temperature whereas the pervaporation is carried out at elevated temperature. Therefore, in a further aspect of the invention, the heat obtained in cooling the reactants in the ketalisation reaction is used to heat up the equilibrium mixture containing the ketal prior to pervaporation.

The following Example further illustrates the process of this invention.

EXAMPLE

Figure 1:
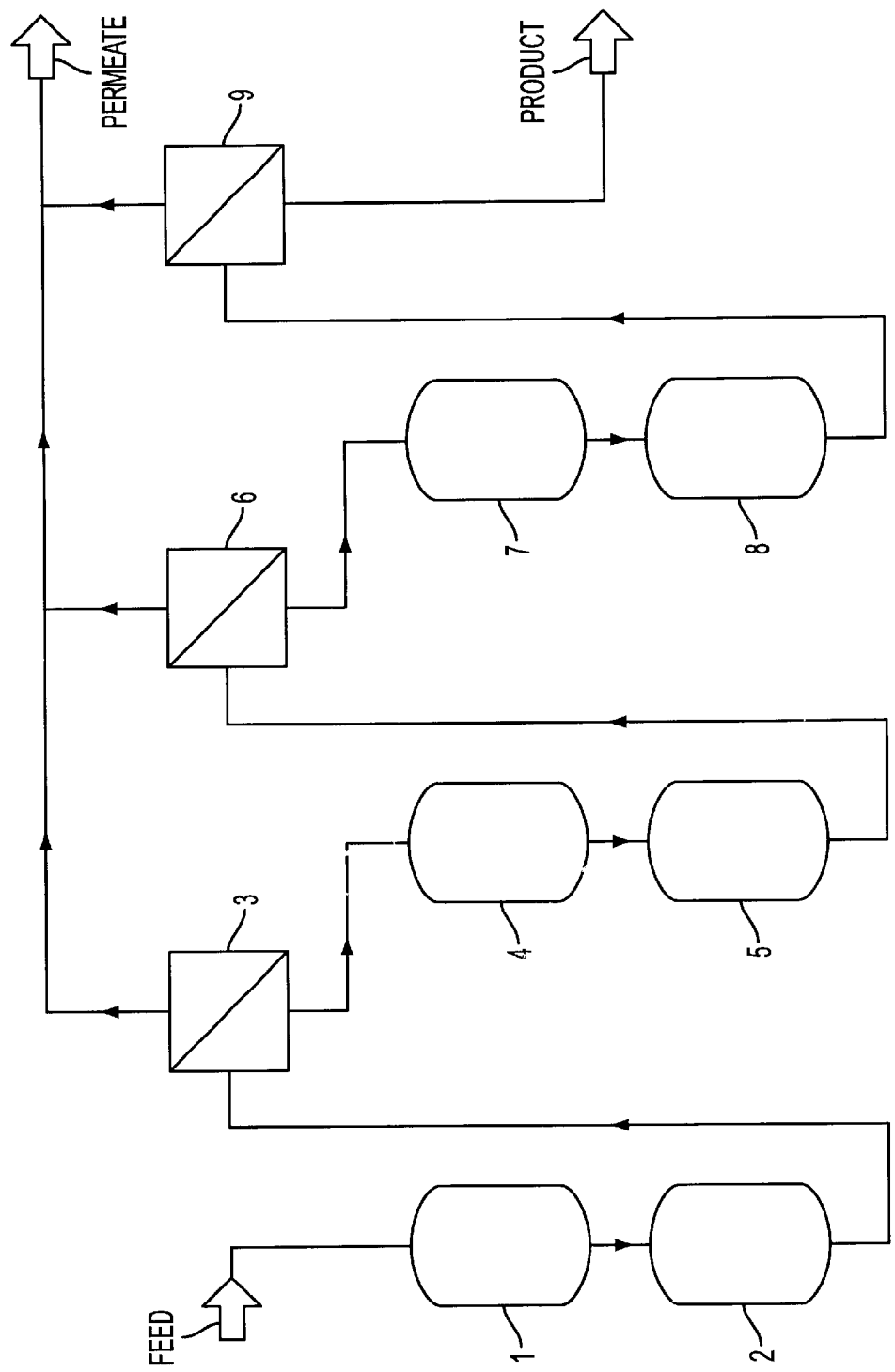
FIG. 1 shows three reaction steps it is to be understood that the process of this invention is not so limited. Depending on the reaction components involved and the requirements concerning the purity of the desired ketal one or more reaction steps may be appropriate. In the preparation of 2,2-dimethoxy propane, 3 or 4 reaction steps suffice to obtain a product of the desired purity as required for the further use of the product.
Figure 1:
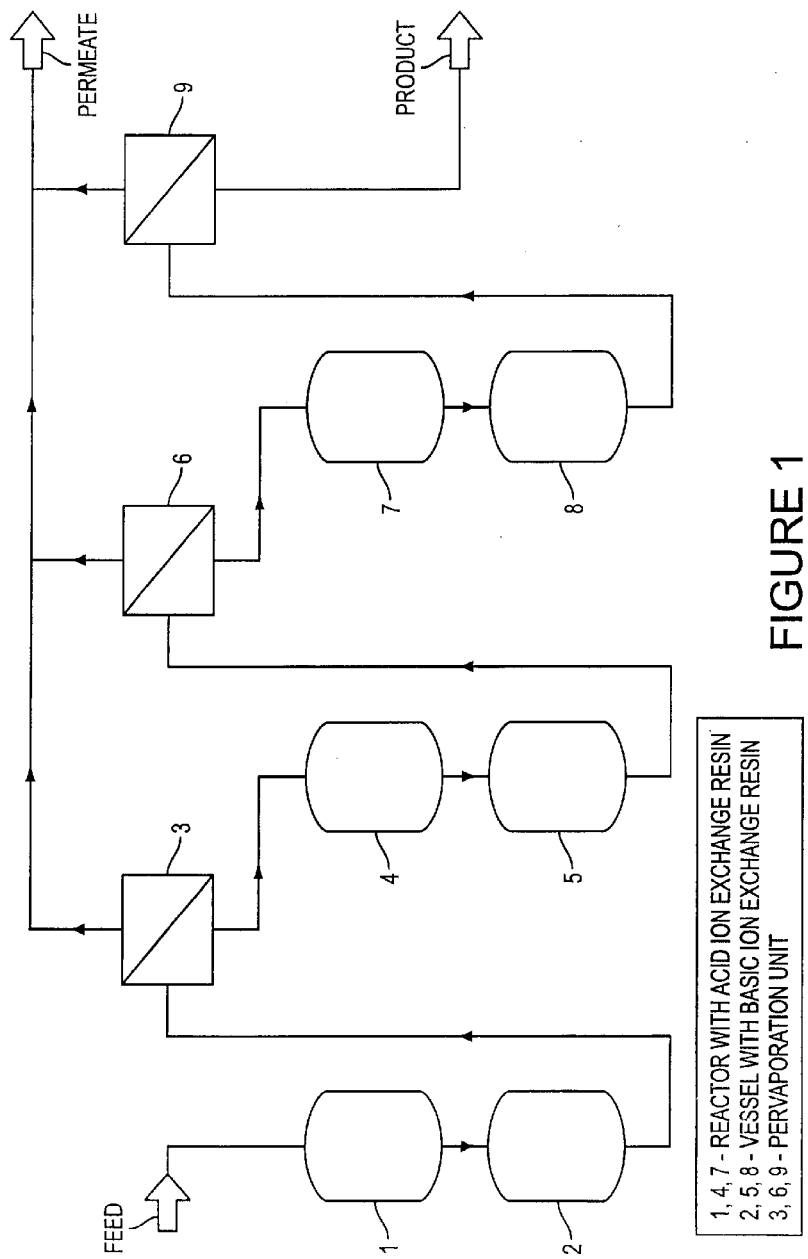

A mixture consisting of 70 wt % of methanol (factory regenerate; corrsponding to ca. 63 wt % of pure methanol) and 30 wt % of acetone was fed into reactor 1 of an equipment corresponding to the one shown in FIG. 1 but consisting of four units (one unit=reactor with acid ion exchange resin, vessel with basic ion exchange resin, and pervaporation unit) with a flow rate of 1.0 kg per hour. The reactors with acid ion exchange resin had a volume of a volume of ca. 0.7 L and were charged with 530 g of AMBERLYST A 15. The vessels with basic exchange resin had a volume of 0.17 L and were charged with 120 g of AMBERLITE IRA 96. The reactors and the connecting tubes were made of glass except the pervaporation unit and the tubes leading from the temperature in the reactors charged with acid ion exchange resin was adjusted to maintain an exit temperature of −34° C. to −36° C. In the pervaporation units the membrane surface was 0.1 m$^2$; the temperature was adjusted to 84° C.; the pressure at the side of the retentate (i.e., before the membrane) was 4 bar (abs.), the pressure at the side of the permeate (i.e., behind the membrane) was 30–38 mbar. Membranes of the type CMC-CE-02 (CM-Celfa) were used. The results obtained are given in the Table below:

| Reaction Step | 1 | 2 | 3 | 4 |
| --- | --- | --- | --- | --- |
| chem. yield of ketal, cumulated | 35.8% | 42.5% | 45.7% | 45.9% |
| chem. yield of ketal per step | 35.8% | 11.6% | 5.6% | 0.4% |
| isol. yield of ketal, cumulated | 35.3% | 42.0% | 44.9% | 44.9% |
| water content | 0.70% | 0.40% | 0.12% | 0.10% |
| ketal content | 29.54% | 43.33% | 52.40% | 56.92% |
| retentate/feed ratio | 70.85% | 57.41% | 50.80% | 46.77% |

"chem(ical) yield" means % of theoretical (100%) yield
"isol(ated) yield" means yield in retentate of individual process step (effective yield that can be used)
retentate/feed ratio means retentate obtained in individual process step based on mass flow fed into the first reactor.

What is claimed is:

1. An apparatus for carrying out a process for the preparation of acetals or ketals by reacting an aldehyde or ketone with an alcohol in the presence of a solid acid, and removing water from the reaction product by pervaporation comprising a reactor containing a solid acid having an inlet and an outlet, a vessel containing a solid base having an inlet and an outlet, and a pervaporation unit having a membrane which is permeable for water and having an inlet and an outlet, wherein the reactor outlet is in fluid communication with the vessel inlet, and the vessel outlet is in fluid communication with the pervaporation unit inlet.

2. The apparatus according to claim 1, which comprises 3 consecutively arranged units each consisting of reactor (1), vessel (2) and pervaporation unit (3).

* * * * *

UNITED STATES PATENT AND TRADEMARK OFFICE
CERTIFICATE OF CORRECTION

PATENT NO. : 6,528,025 B1
DATED : March 4, 2003
INVENTOR(S) : Volkmar Boesch and Juan Ramon Herguijuela It is certified that error appears in the above-identified patent and that said Letters Patent is hereby corrected as shown below:

<u>Title page, Item [54] and Column 1, line 1,</u>
Please change "OF" to -- AND --;

<u>Title page,</u>
Item [57], ABSTRACT,
Line 2, please change "Ketone" to -- ketone --.

Signed and Sealed this

Nineteenth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,528,025 B1
DATED        : March 4, 2003
INVENTOR(S)  : Boesch et al.

It is certified that error appears in the above-identified patent and that said Letters Patent is hereby corrected as shown below:

<u>Drawings,</u>
Delete drawing sheet consisting of Fig. 1, and substitute therefore the drawing sheet consisting of Fig 1 as shown on the attached page.

Signed and Sealed this

Seventeenth Day of February, 2004

JON W. DUDAS
*Acting Director of the United States Patent and Trademark Office*